Jan. 29, 1974 G. H. MACK ET AL Plant Pat. 3,454
CHRYSANTHEMUM PLANT
Filed May 15, 1972
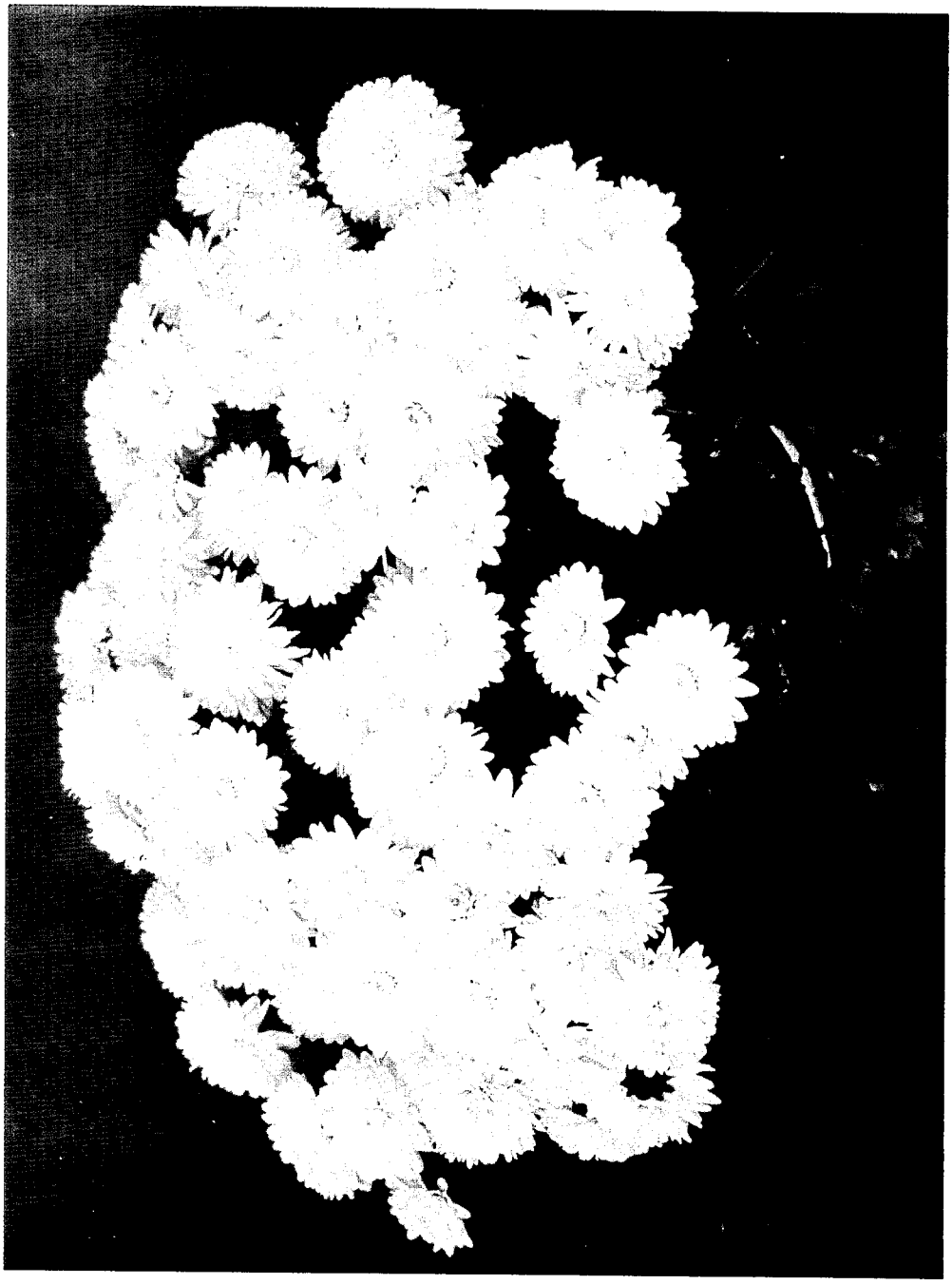

United States Patent Office

Plant Pat. 3,454

Patented Jan. 29, 1974

3,454

CHRYSANTHEMUM PLANT

Grace H. Mack, 108 Wahackme Road, New Canaan, Conn. 06840, and Walter H. Jessel, Jr., Doylestown, and William E. Duffett, Akron, Ohio; said Jessel and said Duffett assignors to said Mack, New Canaan, Conn.

Filed May 15, 1972, Ser. No. 253,641
Int. Cl. A01h *5/00*
U.S. Cl. Plt.—75 1 Claim

The present invention comprises a new and distinct cultivar of chrysanthemum plant which is a seedling of parents identified as #C84–62 × #MX514–63. Both parents are unpatented and identified for breeding purposes by the above breeding numbers to distinguish the parents from other parents in the breeding program.

The new cultivar is similar in many respects to the unpatented but commercial cultivar Early Gold, having the same characteristics as Early Gold of:

(1) Early response.
(2) Flower form.
(3) Foliage size and color.
(4) Compact cushion habit.
(5) Flowering period.

The new cultivar is distinguished from Early Gold by the following characteristics when grown under comparable conditions:

(1) Flowers approximately ¼″ larger.
(2) Individual petals are incurved with a longitudinal petal roll, thereby providing a more solid flower and a more formal flower form.

(3) Approximately six days longer keeping quality in the fall garden.
(4) A lighter gold flower color.
(5) Stronger stems.
(6) A taller, more spreading habit with slightly more prolific branching in the fall garden.
(7) Less leaf serration.
(8) More prominent stipules.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and the following detailed description is based on observations made of the new cultivar at and in a greenhouse in Barberton, Ohio. The response time, blooming period, color, and total vigor may vary significantly with varying environmental conditions such as temperature, day length, and light intensity. Suggested flowering in the northern and western United States and coastal California is from mid-April through May and mid-September through mid-October.

The accompanying drawing shows the unique characteristics of the new cultivar, the color being as nearly true as possible with color illustrations of this type.

In the following description, color references are made to the Munsell Color Book, 1963 edition, and comparisons are made with the cultivar Early Gold. Where only a single value or description appears for the new cultivar, the same value or description applies also to the comparison cultivar.

Botanical classification: *Chrysanthemum morifolium*

| | Pixie Cushion | Early Gold |
|---|---|---|
| Bloom: | | |
| Size | 1⅛″ | 1¼″. |
| Fully expanded | 1¾″ | 1⅝″. |
| Borne | Clusters on elongated pedicels | Clusters on elongated pedicels. |
| Stems | Strong | Moderately strong. |
| Form | Intermediate pompon | |
| Permanence | 14–16 days | 10 days. |
| Color: | | |
| Center of flower | Dark yellow, 6.25Y8.5/12 | Dark yellow, 5Y8.5/12. |
| Base of petals | Yellow, 7.5Y8.5/10 | Do. |
| Inside of petals | do | Do. |
| Reverse of petals | Light yellow, 7.5Y8.5/8 | Yellow, 5Y8.5/10. |
| Tonality from a distance | Yellow | Yellow. |
| Discoloration | Yellow, 7.5Y8.5/8 | Yellow, 5Y8.5/8. |
| Petals: | | |
| Texture | Smooth | |
| Appearance and form | Open at base, broad shallow ridged keel—slight lateral roll, tapering to a blunt point. | Open at base, broad shallow slightly ridged keel, tapering to a blunt point. |
| Arrangement | Composite, whorled on a single receptacle | |
| Persistence | Resist shatter | |
| Fragrance | Typical chrysanthemum | |
| Reproductive organs: | | |
| Stamen, anthers | 5–10 | 4–5. |
| Pollen | None—very scant | None. |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Compact—spreading | |
| Height | Approximately 9½″ from a mid-June, outdoor, natural season planting; single pinch. | Approximately 8″ from a mid-June, outdoor, natural season planting; single pinch. |
| Spread | Approximately 16″ from a mid-June, outdoor, natural season planting; single pinch. | Approximately 14″ from a mid-June, outdoor, natural season planting; single pinch. |
| Foliage: | | |
| Top side | Dark green, 7.5GY3/4 | Dark green, 7.5GY3/4. |
| Size | 2¼″ long, 1½″ wide | 2½″ long, 1½″ wide. |
| Quantity | Numerous | |
| Shape | Spatulate lobed | |
| Texture | Smooth | |
| Ribs & veins | Prominent | |
| Edge | Moderately indented | |
| Serration | Very slight | Moderate. |
| Underside | Light green, 7.5GY5/4 | Light green, 7.5GY5/4. |
| Stipules | Prominent | Rudimentary. |

We claim:

1. A new and distinct cultivar of chrysanthemum characterized particularly as to its uniqueness when compared with the garden cultivar Early Gold by its flowers which are approximately ¼″ larger; its stronger stems; its incurved individual petals with a longitudinal petal roll, thereby providing a more solid flower and a more formal flower form; its approximately six days longer keeping quality in the fall garden; its lighter gold flower color; its taller, more spreading habit with slightly more prolific branching in the fall garden, less leaf serration, and more prominent stipules.

No references cited.

ROBERT E. BAGWILL, Primary Examiner